United States Patent
Askenazi et al.

(10) Patent No.: US 12,402,865 B2
(45) Date of Patent: Sep. 2, 2025

(54) URINE COLLECTION SYSTEM

(71) Applicants: THE UAB RESEARCH FOUNDATION, Birmingham, AL (US); The Children's Hospital of Alabama, Birmingham, AL (US)

(72) Inventors: David Askenazi, Birmingham, AL (US); Lynn Dill, Birmingham, AL (US); Martin Dawson Holland, Birmingham, AL (US); Shelby Leverett, Birmingham, AL (US); Elizabeth Dechant, Birmingham, AL (US)

(73) Assignees: The UAB Research Foundation, Birmingham, AL (US); The Children's Hospital of Alabama, Birmingham, AL (US)

( * ) Notice: Subject to any disclaimer, the term of this patent is extended or adjusted under 35 U.S.C. 154(b) by 348 days.

(21) Appl. No.: 17/774,462

(22) PCT Filed: Nov. 13, 2020

(86) PCT No.: PCT/US2020/060541
§ 371 (c)(1),
(2) Date: May 4, 2022

(87) PCT Pub. No.: WO2021/097310
PCT Pub. Date: May 20, 2021

(65) Prior Publication Data
US 2022/0387001 A1 Dec. 8, 2022

Related U.S. Application Data

(60) Provisional application No. 62/934,787, filed on Nov. 13, 2019.

(51) Int. Cl.
*A61B 10/00* (2006.01)
*A61F 5/455* (2006.01)

(52) U.S. Cl.
CPC ............ *A61B 10/007* (2013.01); *A61F 5/455* (2013.01)

(58) Field of Classification Search
CPC .............................. A61B 10/007; A61F 5/455
(Continued)

(56) References Cited

U.S. PATENT DOCUMENTS 3,114,916 A * 12/1963 Hadley ................. A61F 5/455
4/144.3
3,227,162 A    1/1966 Machuca Everardo
(Continued)

FOREIGN PATENT DOCUMENTS

CN    202920436 U    5/2013
CN    204394771 U    6/2015
(Continued)

OTHER PUBLICATIONS

Y. Skvortsova "Written Opinion of the International Searching Authority and International Search Report", PCT/US2020/060541, Federal Institute of Industrial Property, Russia; Feb. 4, 2021.
(Continued)

*Primary Examiner* — Andrew J Mensh
(74) *Attorney, Agent, or Firm* — Nicholas J. Landau; Maynard Nexsen PC

(57) ABSTRACT

A urine collection device is provided. The urine collection device includes a basin configured to fit a perineal region of a female human subject and to receive urine; a lip attached to the basin and having a contact surface for attachment to the perineal region; a ridge extending into the basin and disposed along an inferior portion of the lip to prevent leakage of urine from the basin; and a drain opening in the
(Continued)

basin for draining the urine. The urine collection device advantageously prevents leakage and allows for easy access for urine analysis and measurement of urine output. Methods and systems for collecting and quantifying urine are also provided.

27 Claims, 10 Drawing Sheets

(58) Field of Classification Search
USPC .......................................................... 604/326
See application file for complete search history.

(56) References Cited

U.S. PATENT DOCUMENTS

| | | | |
|---|---|---|---|
| 3,340,876 A * | 9/1967 | Hill .......................... | A61F 5/451 600/580 |
| 3,401,697 A | 9/1968 | Raffensperger et al. | |
| 4,194,508 A * | 3/1980 | Anderson ................ | A61F 5/455 4/144.3 |
| 4,198,979 A * | 4/1980 | Cooney ................... | A61F 5/455 604/329 |
| 4,233,977 A | 11/1980 | Mattson | |
| 4,496,355 A * | 1/1985 | Hall ......................... | A61F 5/455 604/327 |
| 4,568,339 A * | 2/1986 | Steer ........................ | A61F 5/455 4/144.3 |
| 4,846,819 A * | 7/1989 | Welch ...................... | A61F 5/455 604/336 |
| 4,911,698 A * | 3/1990 | Wapner ................... | A61B 10/007 4/144.3 |
| 4,936,838 A | 6/1990 | Cross et al. | |
| 5,004,463 A | 4/1991 | Nigay | |
| 5,616,138 A | 4/1997 | Propp | |
| 5,632,736 A | 5/1997 | Block | |
| 5,893,176 A * | 4/1999 | Magiera ................. | A61F 5/4556 4/144.3 |
| 10,335,121 B2 | 7/2019 | Desai | |
| 10,842,468 B2 | 11/2020 | Park et al. | |
| 11,246,573 B2 | 2/2022 | Duval | |
| 2006/0178649 A1 | 8/2006 | Ma | |
| 2012/0103347 A1 | 5/2012 | Wheaton et al. | |
| 2014/0325746 A1 | 11/2014 | Block | |
| 2016/0030228 A1* | 2/2016 | Jones ....................... | A61F 5/455 604/329 |
| 2016/0051176 A1* | 2/2016 | Ramos ................... | G01F 23/265 600/573 |
| 2016/0354230 A1 | 12/2016 | Abuhaikal | |
| 2017/0281399 A1 | 10/2017 | Vanmiddendorp et al. | |
| 2018/0188097 A1 | 7/2018 | Levine | |
| 2020/0060541 A1 | 2/2020 | Andrade et al. | |

FOREIGN PATENT DOCUMENTS

| | | | | |
|---|---|---|---|---|
| CN | 205094753 U | 3/2016 | | |
| EP | 2351542 A1 | 8/2011 | | |
| EP | 2642957 B1 | 2/2013 | | |
| FR | 0890349 A1 * | 1/2013 | ............. | A61F 5/455 |
| GB | 1422638 A | 1/1976 | | |
| JP | S55-093040 A | 7/1980 | | |
| JP | S59-072538 U | 5/1984 | | |
| JP | S64-68258 A | 3/1989 | | |
| JP | H03-501812 A | 4/1991 | | |
| JP | 2012-531253 A | 12/2012 | | |
| JP | 2019-512672 A | 5/2019 | | |
| JP | 2019-520553 A | 7/2019 | | |
| WO | 2000040180 A1 | 7/2000 | | |
| WO | 2003079942 A1 | 10/2003 | | |
| WO | 2005/089687 A2 | 9/2005 | | |
| WO | 2005/107602 A1 | 11/2005 | | |
| WO | 2006/077350 A1 | 7/2006 | | |

OTHER PUBLICATIONS

Office Action received for Canadian Patent Application No. 3157318, mailed on Aug. 10, 2023, 04 pages.

Extended European Search Report received for European Patent Application No. 20886532.9, mailed on Sep. 8, 2023, 07 pages.

International Preliminary Report on Patentability received for International Patent Application No. PCT/US2020/060541, mailed on May 27, 2022, 06 pages.

Kellum et al., "Diagnosis, evaluation, and management of acute kidney injury: a KDIGO summary (Part 1)", Crit Care, vol. 17, No. 1, Article No. 204, 2013, pp. 1-15.

Sutherland et al., "Fluid overload and mortality in children receiving continuous renal replacement therapy: the prospective pediatric continuous renal replacement therapy registry", American journal of kidney diseases : the official journal of the National Kidney Foundation, vol. 55, No. 2, 2010, 316-325.

Rewa et al., "The furosemide stress test for prediction of worsening acute kidney injury in critically ill patients: A multicenter, prospective, observational study", Journal of Critical Care, vol. 52, Aug. 2019, pp. 1-18.

Basu et al., "Renal angina: an emerging paradigm to identify children at risk for acute kidney injury", Pediatric nephrology, vol. 27, No. 7, 2012, 1067-1078.

Endre et al., "Differential diagnosis of AKI in clinical practice by functional and damage biomarkers: workgroup statements from the tenth Acute Dialysis Quality Initiative Consensus Conference", Contrib Nephrol, vol. 182, 2013, pp. 30-44.

Ostermann et al., "Clinical review: Biomarkers of acute kidney injury: where are we now?", Crit Care, vol. 16, No. 5, 2012, pp. 1-13.

Siegel et al., "Impact of a Daily PICU Rounding Checklist on Urinary Catheter Utilization and Infection", Pediatr Qual Saf, vol. 3, No. 3, e078, 2018, pp. 1-6.

Mariano et al., "Furosemide as a functional marker of acute kidney injury in ICU patients: a new role for an old drug", J Nephrol, vol. 32, No. 6, Dec. 2019, pp. 883-893.

Diamond et al., "Influence of volume expansion, serum sodium, and fractional excretion of sodium on urate excretion", Pflugers Arch., vol. 356, No. 1, 1975, pp. 47-57.

Stanski et al., "Integration of urinary neutrophil gelatinase-associated lipocalin with serum creatinine delineates acute kidney injury phenotypes in critically ill children", Journal of Critical Care, vol. 53, Oct. 2019, pp. 1-7.

Kaddourah et al., "Oliguria and Acute Kidney Injury in Critically Ill Children: Implications for Diagnosis and Outcomes", Pediatr Crit Care Med, vol. 20, No. 4, 2019, pp. 332-339.

Biological Evaluation Of Medical Devices—Part 1: Evaluation And Testing Within A Risk Management Process, ISO 10993-1:2018 (2018) (Avient Corporation, Avon Lake, OH, USA).

Office Action received for Japanese Patent Application No. 2022-525515, mailed on Apr. 23, 2024, 7 pages including English translation.

Search Report received for Japanese Patent Application No. 2022-525515, mailed on Apr. 24, 2024, 48 pages including English translation.

Office Action received for Australian Patent Application No. 2020381525, mailed on Nov. 5, 2024, 07 pages.

* cited by examiner

SECTION B-B

SECTION A-A

SECTION B-B

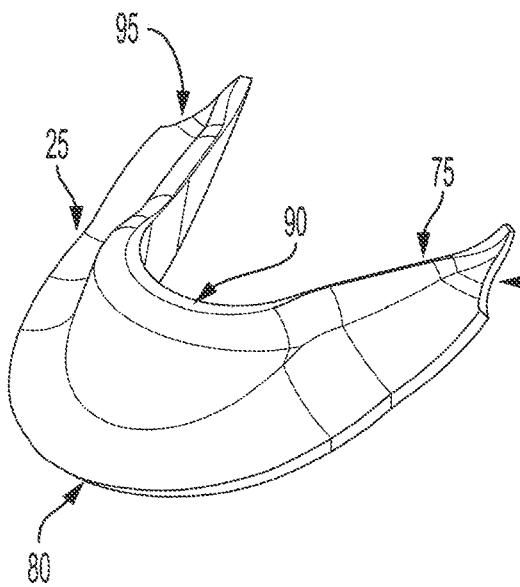
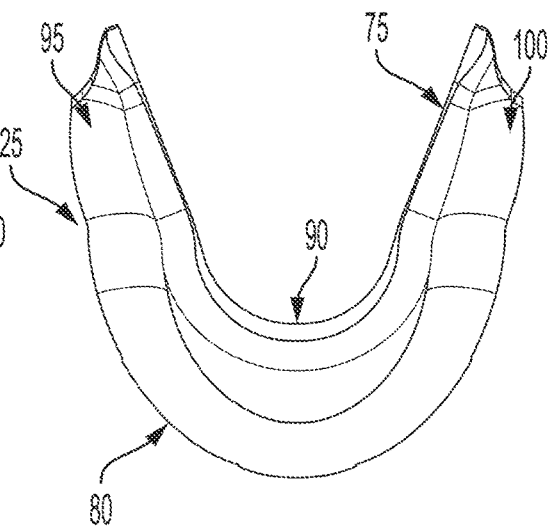
FIG. 5A
FIG. 5B
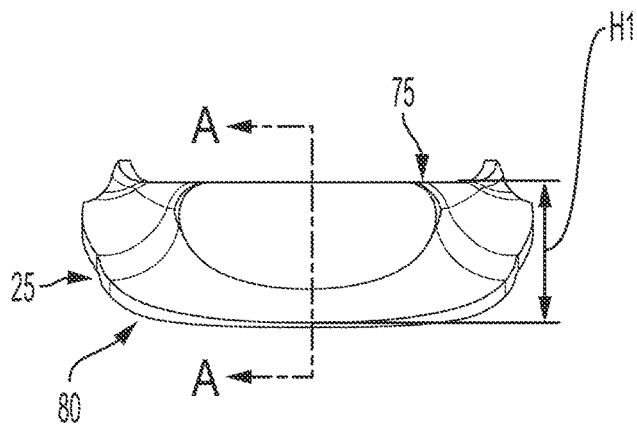
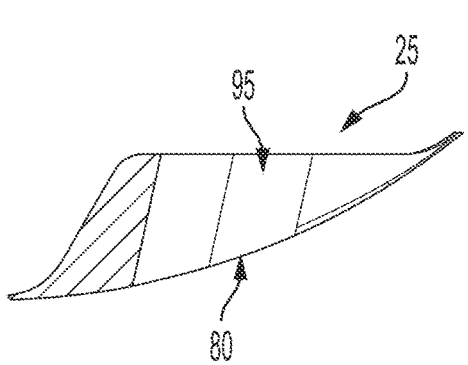
FIG. 5C
SECTION A-A
FIG. 5D
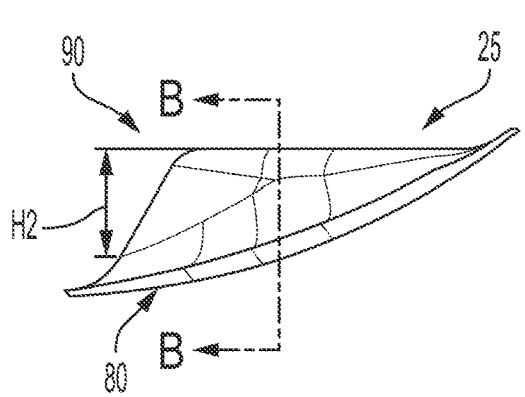
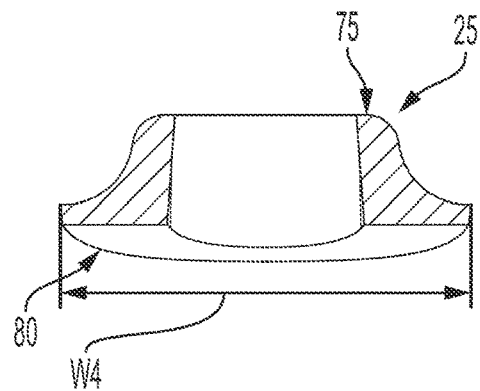
FIG. 5E
SECTION B-B
FIG. 5F

SECTION A-A

URINE COLLECTION SYSTEM

CROSS-REFERENCE TO RELATED APPLICATIONS

This application claims the benefit of U.S. Provisional Application No. 62/934,787, filed Nov. 13, 2019 under the laws of the United States of America and other countries.

BACKGROUND

Field of the Disclosure

The present disclosure relates generally to urine collection systems. More particularly, this disclosure relates to a urine collection system for pediatric patients.

Background

Measurement of accurate fluid intake and output is part of the care of hospitalized adults, children and neonates. The need for accurate urine output assessment is present in both the ICU and non-ICU settings. Unfortunately, in neonates and small children, this information is often not available or unreliable. The clinician relies on accurate and timely urine output quantification to make medical assessments and prescribe interventions to maintain appropriate fluid homeostasis in critically ill patients. A urine collection system that can reliably capture urinary output (UOP) is needed to improve care for neonates and small children.

Unfortunately, a safe, easy-to-use, effective urine collection system for neonates and small children has not been developed. Indeed, placement of an indwelling catheter is extremely difficult in small babies, and is associated with catheter—associated urinary tract infections (CAUTI). Additionally, currently available external urine collection systems (bags) are not ideal, as they must be changed out after each void, often leak, and can harm small infants who have extremely fragile and sometimes paper-thin skin. Moreover, the use of diaper weights is difficult when mixed with stool and does not allow for urine analysis. Use of cotton balls in the diaper is associated with inaccurate measurement of protein.

Accordingly, there is an unmet need for a neonatal urine collection system that is safe, easy to use, continuously measures UOP, and allows for easy sampling of urine.

SUMMARY

A non-invasive urine collection system has been developed capable of collecting all of the patient's urine output and being safely fastened to delicate pediatric patients. The following presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

In a first aspect, a urine collection device is provided, the urine collection device comprising: a basin configured to fit a perineal region of a female human subject and to receive urine; a lip attached to the basin and having a contact surface for attachment to the perineal region; a ridge extending away from the interior of the basin and disposed along an inferior portion of the device to prevent leakage of urine from the basin; and a drain opening in the basin for draining the urine.

In a second aspect, a urine collection device is provided, the urine collection device comprising: a basin configured to fit a perineal region of a female human subject and to receive urine; a lip attached to the basin and having a surface area sufficient to adhere the device to the female human subject using an adhesive; a ridge on an inferior end of the basin to prevent leakage of urine from the basin; and a drain opening in the basin for draining the urine.

In a third aspect, a urine collection device for use by a female pediatric subject is provided, the urine collection device comprising: a basin having a bowl and a rim, the bowl dimensioned to cover the subject's urethra and the rim dimensioned to contact a region surrounding the urethra; a lip extending radially from the rim of the basin and configured to contact the subject's abdomen or mons pubis; a ridge extending away from the bowl of the basin on an inferior side of the basins, the ridge configured to create a seal by extending between the subject's labia; and a drain opening positioned on the basin for draining urine from the basin.

In a fourth aspect, a method of collecting urine excreted by an infant is provided, the method comprising: attaching any of the urine collection devices described above to a perineal region of the infant, wherein an adhesive is on the lip; and collecting urine excreted by the infant in the urine collection device.

In a fifth aspect, a method of measuring urine excreted by an infant is provided, the method comprising: attaching any of the urine collection devices described above to a perineal region of the infant; collecting urine excreted by the infant in the urine collection device; and quantifying the urine.

In a sixth aspect, a system for collecting and measuring urine excreted by a pediatric female subject is provided, the system comprising: any of the urine collection devices described above; and an adhesive on the lip of the urine collection device.

BRIEF DESCRIPTION OF THE DRAWINGS

Further features and advantages can be ascertained from the following detailed description that is provided in connection with the drawings described below:

FIG. 5A is a front perspective view of a ridge of the urine collection device according to an exemplary embodiment of the present disclosure.

FIG. 5B is a top view of the ridge shown in FIG. 5A.

FIG. 5C is a front view of the ridge shown in FIG. 5A.

FIG. 5D is a cross sectional view of the ridge shown in FIG. 5C taken along the line "A-A."

FIG. 5E is a side view of the ridge shown in FIG. 5A.

FIG. 5F is a cross sectional view of the ridge shown in FIG. SE taken along the line "B-B."

DETAILED DESCRIPTION

Definitions

Figure 1A:
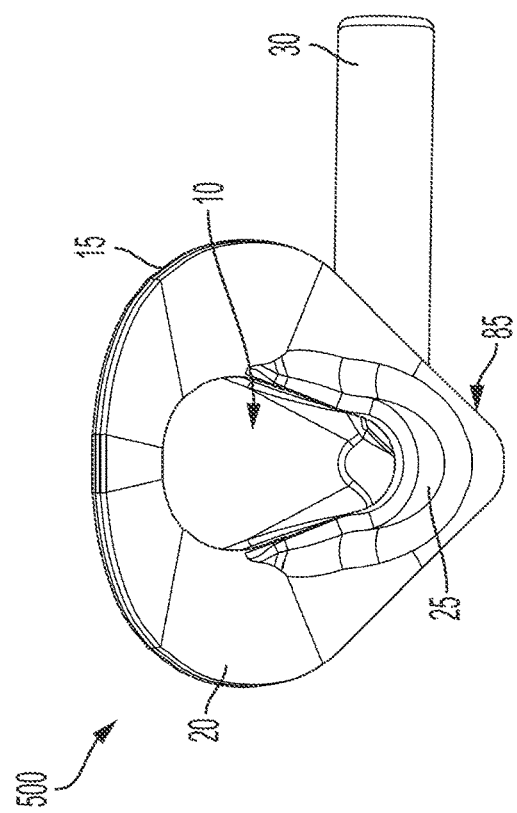
FIG. 1A is a front perspective view of a urine collection device according to one embodiment of the present disclosure.
Figure 1B:
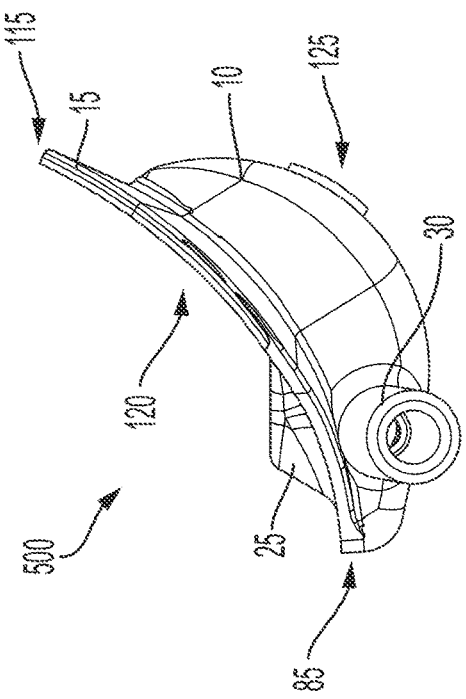
FIG. 1B is a top view of the urine collection device shown in FIG. 1A.
Figure 1C:
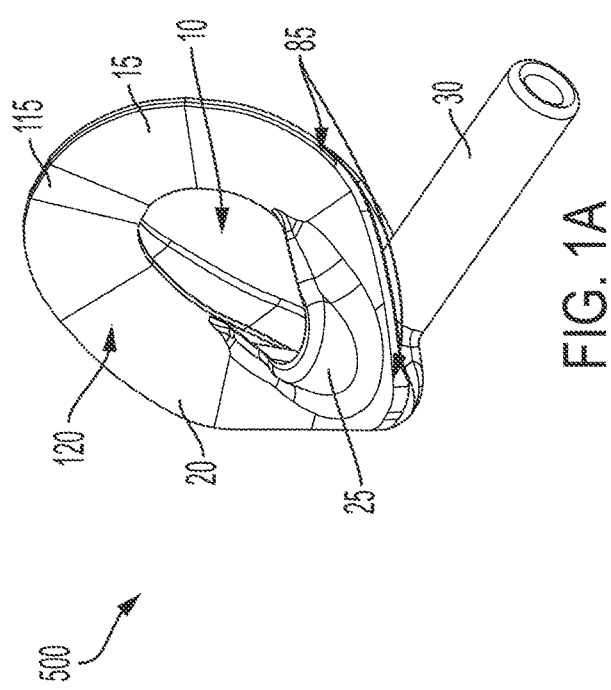
FIG. 1C is a front view of the urine collection device shown in FIG. 1A.
Figure 1D:
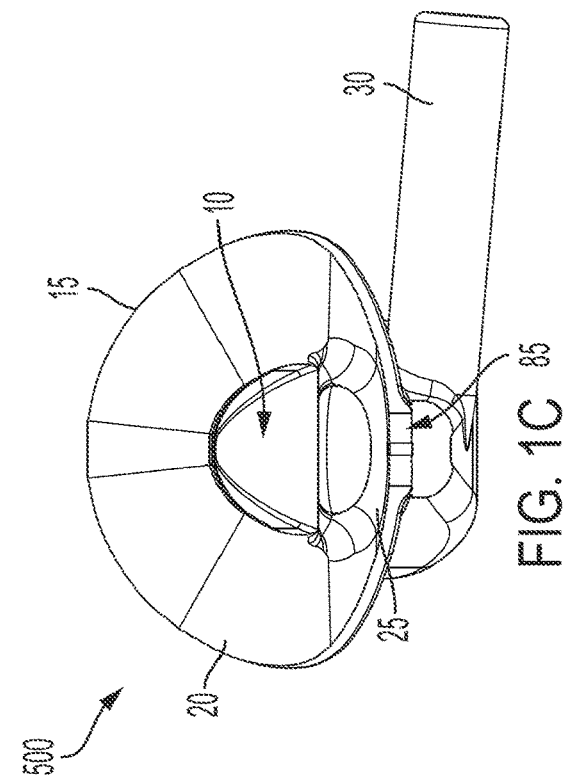
FIG. 1D is a side view of the urine collection device shown in FIG. 1A.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given herein are approximate unless stated otherwise, meaning that the term "about" or "approximately" can be inferred when not expressly stated.

The terminology used herein is for the purpose of describing particular embodiments only and is not intended to be limiting. As used herein, the singular forms "a," "an," and "the" are intended to include the plural forms as well (i.e., at least one of whatever the article modifies), unless the context clearly indicates otherwise.

With reference to the use of the word(s) "comprise" or "comprises" or "comprising" in the foregoing description and/or in the following claims, unless the context requires otherwise, those words are used on the basis and clear understanding that they are to be interpreted inclusively, rather than exclusively, and that each of those words is to be so interpreted in construing the foregoing description and/or the following claims.

The term "consisting essentially of" means that, in addition to the recited elements, what is claimed may also contain other elements (steps, structures, ingredients, components, etc.) that do not adversely affect the operability of what is claimed for its intended purpose. Such addition of other elements that do not adversely affect the operability of what is claimed for its intended purpose would not constitute a material change in the basic and novel characteristics of what is claimed.

Terms such as "at least one of A and B" should be understood to mean "only A, only B, or both A and B." The same construction should be applied to a longer list (e.g., "at least one of A, B, and C").

The terms "first", "second", "third," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

When reference is made to physiological directions, axes, and planes these should be construed to refer to the applicable directions, axes, and planes when the device is properly placed on the patient.

Urine Collection Device and System

Devices, systems, and method of collecting and measuring urine are disclosed herein. Appropriate urine output assessment is useful for adequate prescription of enteral or parental fluid provision. It is useful for quantification of UOP for the diagnosis of acute kidney injury (AKI), fluid overload, furosemide stress test (a test that can delineate kidney injury progression based on the amount of urine output made after a dose of a diuretic), and the renal angina index. Being able to capture urine for diagnostic tests is useful for evaluation of urine electrolytes, fractional excretion of sodium, and novel urine biomarker tests that are actively being investigated in adults, children and neonates.

Embodiments of the urine collection device are designed to fit a female pediatric patient and allow for the collection and quantification of urine. The urine collection device of the present disclosure advantageously prevents leakage and allows for easy access for urine analysis and measurement of urine output. Embodiments of the device may also be securely placed on a patient using an adhesive without irritation or damage to the skin, even when the patient is an infant or a neonate in some cases.

Figure 9:
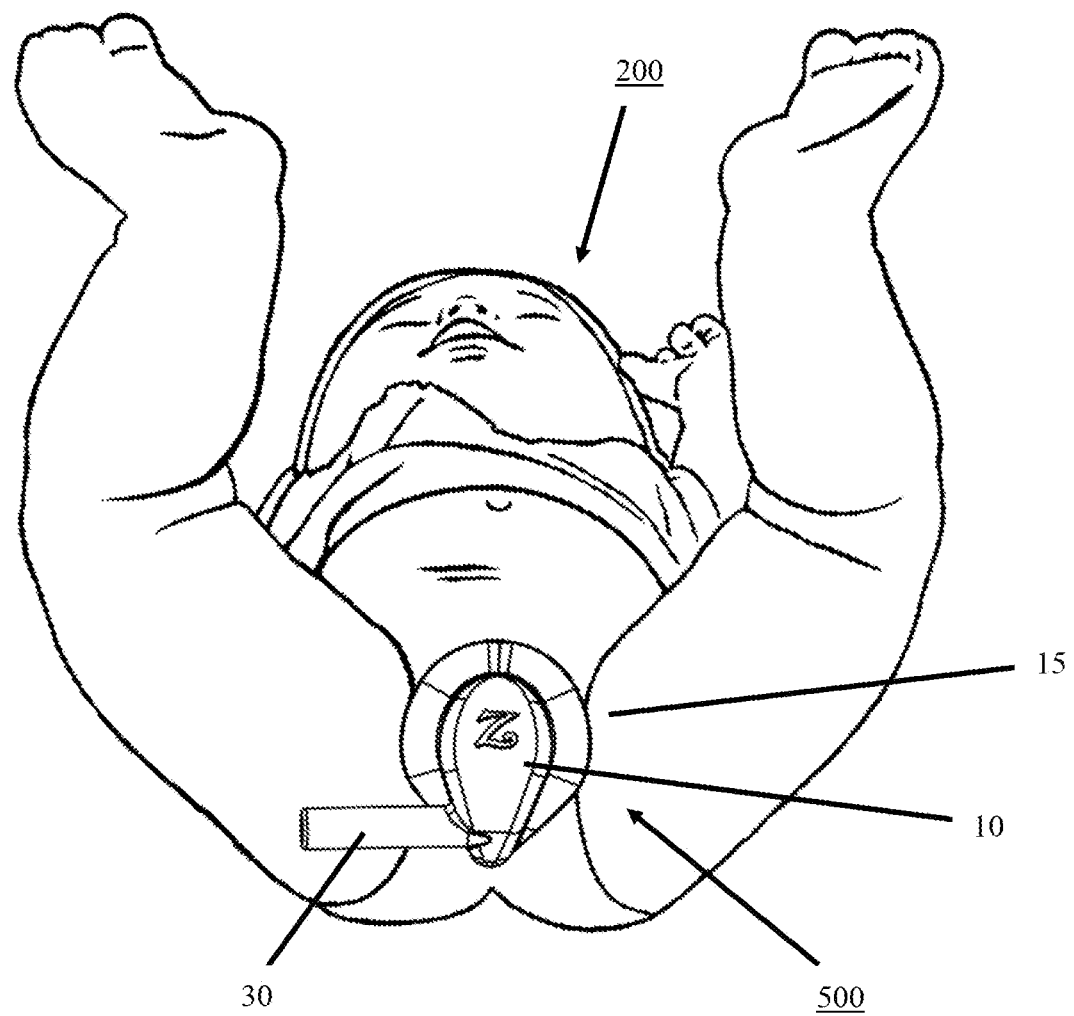
FIG. 9 is a view of an embodiment of the device when in place on a patient.

Referring to FIGS. 1A-1D, a urine collection device 500 according to an embodiment is shown as a non-limiting example. The illustrated embodiment of the urine collection device 500 is configured to be worn externally by a female patient, around the patient's urethra, to collect urine excreted through the urethra, as shown in FIG. 9. In this embodiment, the female patient is a pediatric patient. The term "pediatric" as used herein refers to infants, children, and adolescents from birth up to the age of 18. In another embodiment, the female patient is a toddler. The term "toddler" as used herein refers to infants and children ages 1-5 years. In still another embodiment, the female patient is an infant. An "infant," as used herein, refers to a patient less than 1 year old. In yet another embodiment, the female patient is a neonate. A "neonate," as used herein, refers to a patient less than four weeks old. In a still further embodiment, the female patient is born at a gestational age of at most 37 weeks and has not yet reached an age of four weeks past what would have been full term ("premature neonate").

The embodiment of the device 500 shown in FIGS. 1A-1D includes a basin 10 in which urine excreted by the female patient can be collected. The basin 10 is configured to fit a perineal region of the female patient. As used herein, the term "perineal region" refers to the region between the thighs extending from the mons pubis to the intergluteal cleft and including the urogenital triangle. The basin 10 includes a lip 15 attached thereto that is configured to be adhered to the patient. In the illustrated embodiment, the lip 15 is attached to the rim of the basin 10 and extends radially therefrom. The lip 15 has a contact surface 20 for attachment to the patient's perineal region. The device 500 also includes a ridge 25 extending away from the basin 10. In the illustrated embodiment, the device 500 has a posterior side 120 including a superior end 115 and an inferior end 85. The illustrated embodiment of the ridge 25 is disposed along the inferior end 85 of the device 500 to prevent leakage of urine from the basin 10 during use. For example, the ridge 25 is disposed along the inferior end 85 so that the ridge 25 may extend between the patient's labia to create a waterproof seal. In the illustrated embodiment a drain opening 50 is positioned in the basin 10 for draining the urine. As shown in FIGS. 1A-1D, a conduit 30 may be fluidly coupled to the basin 10 at the drain opening 50 for draining the urine. Once drained, urine may be collected in an external collection container (not shown).

Figure 2:
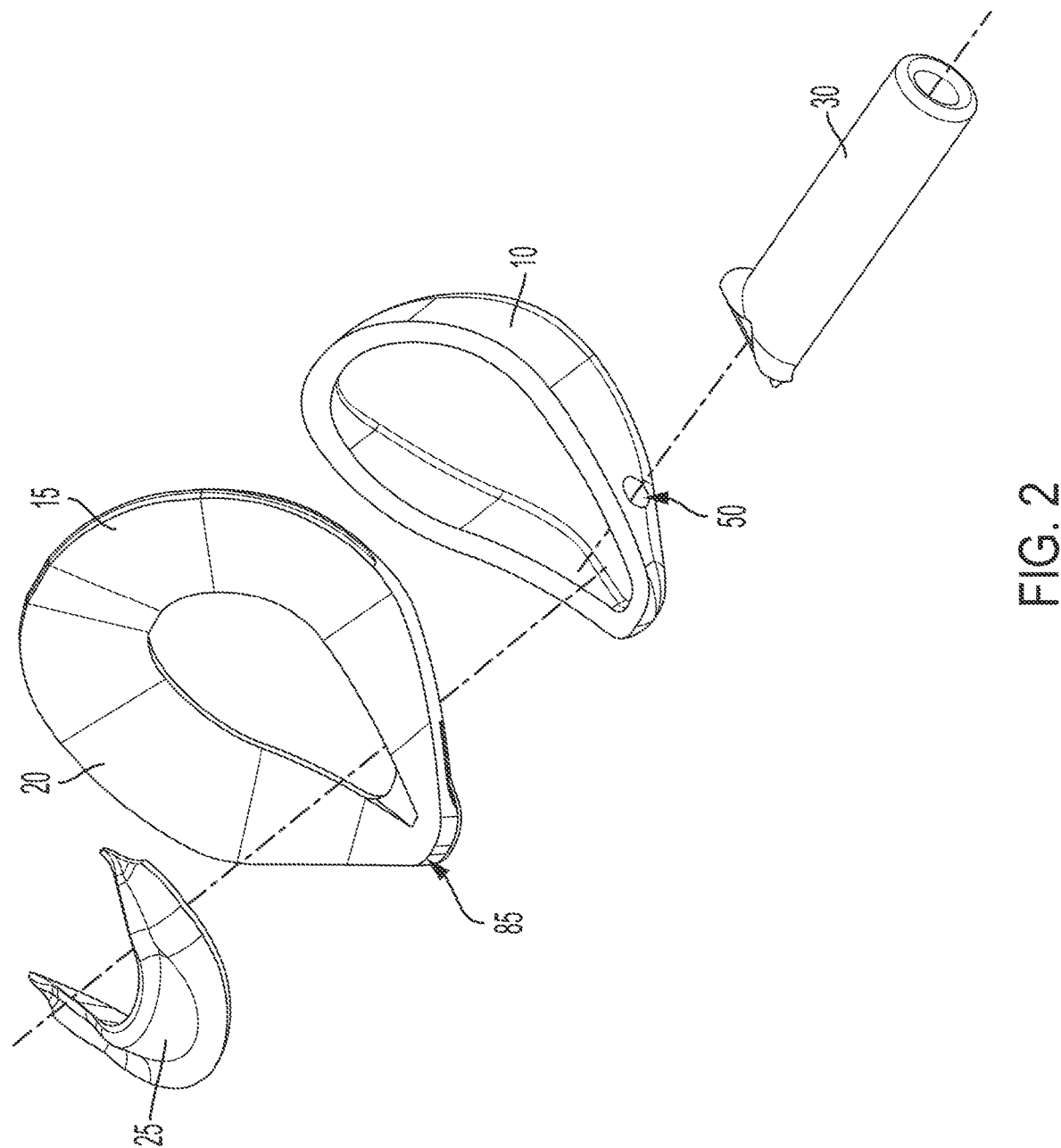
FIG. 2 is an exploded view of the urine collection device shown in FIG. 1A.

FIG. 2 is an exploded view of the embodiment of the urine collection device 500 shown in FIGS. 1A-1D. As illustrated in FIG. 2, the lip 15 is configured for attachment to the rim of the basin 10. In one embodiment, the lip 15 is removably attached to the basin 10. For instance, the lip 15 may be removably attached to the basin 10 by any non-permanent fastening means, such as adhesives, hook and loop fasteners, screws, pins, bolts, or rivets. This allows for easy access to the basin 10 for cleaning and sanitization purposes. In another embodiment, the lip 15 may be integrally formed with the basin 10 such that the lip 15 is not removable from the basin 10.

As shown in FIG. 2, the ridge 25 may be configured for attachment to the inferior end 85 of the lip 15. The ridge 25 may be removably attached to the lip 15 by any fastening means (permanent or impermanent) or the ridge 25 may be integrally formed with the lip 15.

Some embodiments of the basin 10 may include the drain opening 50. The conduit 30 may be fluidly coupled to the basin 10 at the drain opening 50 to allow for drainage of the urine to a separate collection container (not shown). In some embodiments of the device, the conduit 30 can be removably attached to the basin 10 so that other drainage mechanisms may be attached to the basin 10. In alternative embodiments, the conduit 30 may be integrally formed with the basin 10.

Figure 3A:
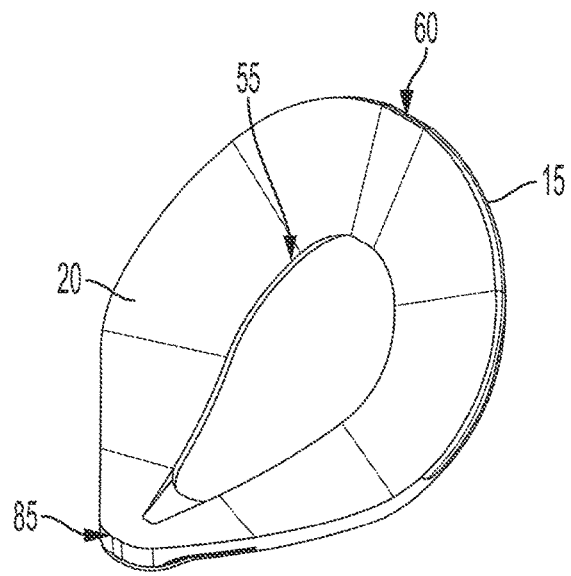
FIG. 3A is a front perspective view of a lip of the urine collection device according to an exemplary embodiment of the present disclosure.
Figure 3B:
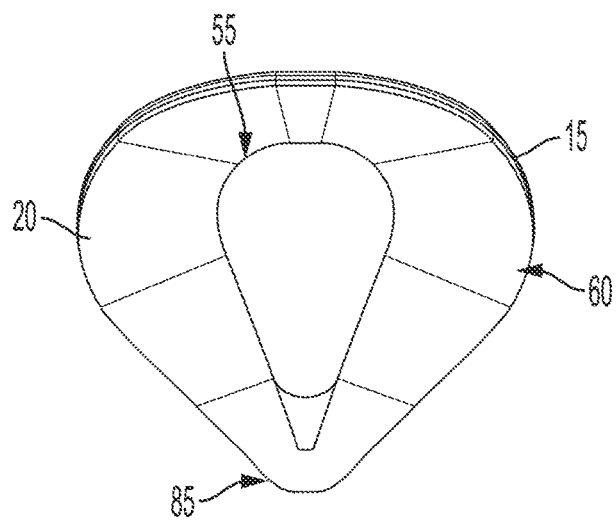
FIG. 3B is a front view of the lip shown in FIG. 3A.

FIGS. 3A-3D illustrate the lip 15 according to an exemplary embodiment of the present disclosure. FIG. 3A is a perspective view of the lip 15 and FIG. 3B is an alternative perspective view of the lip 15. The lip 15 is configured to be adhered to the patient's body around the patient's urethra. The lip 15 forms a liquid-tight seal between the basin 10 and the patient's body to provide a pathway through which urine excreted by the patient can be collected without loss to leaks. The dimensions of the lip 15 can be selected to provide the desired amount of surface area for attaching the urine collection device 500 to the patient's body using an adhesive. For instance, the contact surface 20 of the lip 15 may have a surface area sufficient to form an adhesive bond with the patient's skin to hold the urine collection device 500 in place.

In one embodiment, the contact surface 20 includes an adhesive (not shown) disposed thereon for attachment to the patient. The adhesive is configured to maintain the device in place on the patient and provide a liquid tight seal on the patient's skin to prevent the urine from leaking out of the sides of the lip 15. In another embodiment, an adhesive may be disposed on the side of the lip 15 opposite the contact surface 20. In a specific embodiment, tape is placed across the side of the lip 15 opposite the contact surface 20 and also on the patient's skin to hold the device in place.

The adhesive may be any adhesive that is suitable for use on human skin. Preferred embodiments of the adhesive have one or more properties of being nontoxic, hypoallergenic, non-irritant, medical-grade, and pressure-sensitive. Further preferred embodiments of the adhesive and can provide a liquid tight seal on the patient's body for a predetermined period of time. The adhesive may be selected based on the ease in which the adhesive can be removed from the patient without inflicting one or more of excessive discomfort, pain, or epidermal injury. Some embodiments of the adhesive can be configured to maintain the liquid tight seal in place for a minimum period of time, such as at least 6 hours, 8 hours, 12 hours, or 24 hours.

The adhesive may be a pressure sensitive adhesive that is capable of forming a bond when pressure is applied to secure the contact surface 20 to the patient's skin. For instance, the adhesive may be pressure sensitive tape or a silicone gel adhesive. In some embodiments, the adhesive is a medical grade adhesive, such as a medical grade pressure sensitive adhesive. Examples of suitable adhesive include without limitation: SIMPURITY DERMAPRO waterproof silicone tape (Safe n Simple, Clarkton, Michigan, USA); and P-DERM® PS-2041 (trilaminate consisting of high adhesion silicone gel adhesive, polyurethane film and medical pressure sensitive acrylic—Polymer Science, Inc., Monticello, Indiana, USA).

Figure 3C:
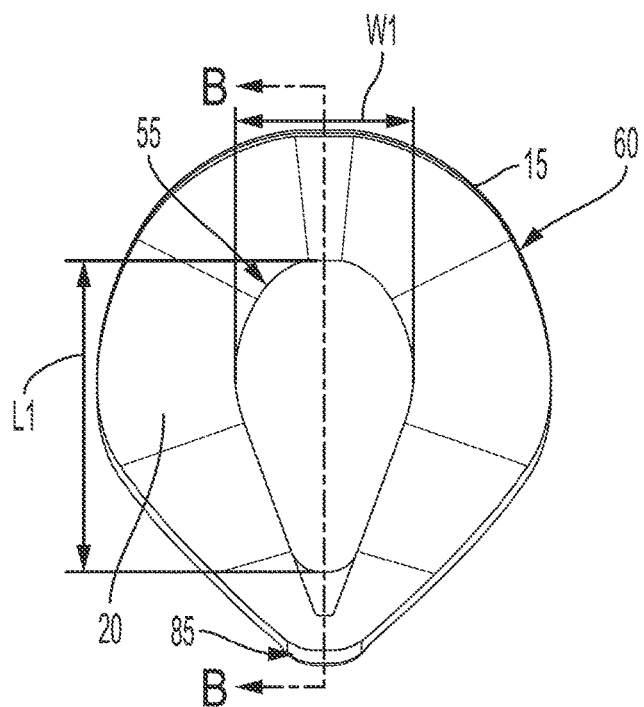
FIG. 3C is a top view of the lip shown in FIG. 3A.

FIG. 3C is an anterior view of the lip 15 according to an exemplary embodiment of the present disclosure. In the embodiment of FIG. 3C the contact surface 20 of the lip 15 is defined by an inner perimeter 55 and an outer perimeter 60. As noted above, the contact surface 20 may be dimensioned to provide a surface area sufficient to form an adhesive bond with the patient's skin. The surface area may be designed based on the adhesive with which it is intended to be used and the adhesive strength needed to maintain the device in place on the patient. The greater the surface area, the greater the potential adhesive strength. Greater surface areas have the further advantage of allowing a gentler adhesive to be used than would be required with a smaller surface area. In some infantile embodiments, the contact surface 20 has a surface area ranging from about 0.5-1.5 square inches (1 sq in=6.452 cm). In further infantile embodiments the contact surface 20 has a surface area ranging from about 0.75-1.25 sq in. In a specific infantile embodiment the contact surface 20 has a surface area of about 0.94 sq in. In other embodiments, the width between the inner perimeter 55 and the outer perimeter 60 may be at least about 0.1 inches. In another embodiment, the width between the inner perimeter 55 and the outer perimeter 60 is at least about 0.2 inches. In still another embodiment, the width between the inner perimeter 55 and the outer perimeter 60 is at least about 0.3 inches.

The inner perimeter 55 of the lip 15 defines an opening of the basin 10. The opening has a length L1 along a vertical axis and a width W1 along a frontal axis. In some embodiments, the width W1 of the opening is at least about 0.40 inches along the frontal axis. In another embodiment, the width W1 of the opening is at least about 0.50 inches along the frontal axis. In still another embodiment, the width W1 of the opening is at least about 0.55 inches along the frontal axis. In other embodiments, the length L1 of the opening is at least about 0.70 inches. In another embodiment, the length L1 of the opening is at least about 0.80 inches. In still another embodiment, the length L1 of the opening is at least about 0.90 inches. In still other embodiments, the length L1 of the opening may be about twice the width W1.

Figure 3D:
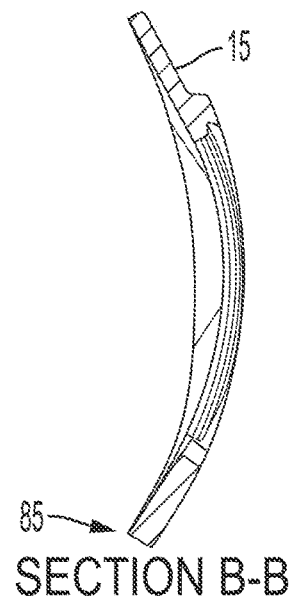
FIG. 3D is a cross sectional view of the lip shown in FIG. 3C taken along the line "B-B."

FIG. 3D is a cross sectional view of the lip 15 illustrated in FIG. 3C taken along the line "B-B." As illustrated in FIG. 3D, the lip 15 is contoured to define a curved surface corresponding to a curvature of the patient's perineal region. The curvature shown in FIG. 3D is advantageous in that it conforms to the anatomical shape of the perineal region, which allows for a more comfortable and secure fit on the patient. In one embodiment, the contact surface 20 of the lip 15 may be contoured to define a concavity. In this embodiment, the lip 15 may have a profile in sagittal cross section of an arc of about 90 degrees to about 140 degrees. In another embodiment, the lip 15 may have a profile in sagittal cross section of an arc of about 100 degrees to about 135 degrees. In still another embodiment, the lip 15 may have a profile in sagittal cross section of an arc of about 110 degrees to about 120 degrees. For instance, the lip 15 may have a profile in sagittal cross section of an arc of about 118 degrees.

Figure 4A:
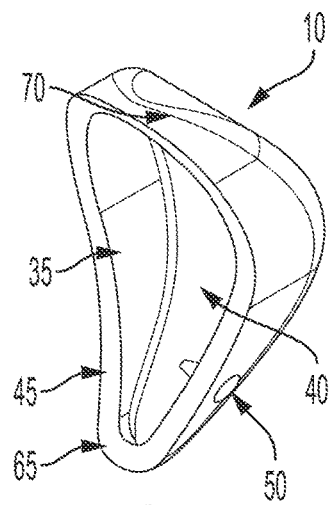
FIG. 4A is a front perspective view of a basin of the urine collection device according to an exemplary embodiment of the present disclosure.

FIGS. 4A-4E illustrate the basin 10 according to an exemplary embodiment of the present disclosure. FIG. 4A is a posterior perspective view of the basin 10. As shown in FIG. 4A, the basin 10 includes a wall 35 defining a bowl 40 where the bowl 40 has a rim 45. The bowl 40 is configured for receiving urine excreted from the female patient. The bowl 40 is shaped and dimensioned to cover the patient's urethra to collect the urine excreted from the patient. In the embodiment shown, the bowl 40 is dimensioned to extend between the patient's legs to a distance at least exceeding the urethra. In a further embodiment, the bowl 40 is dimensioned to extend vertically from the abdomen superior to the urethra between the patient's legs at least to the perineum.

The basin 10 may also include a drain opening 50 in the wall 35 for draining the collected urine. In the illustrated embodiment, the drain opening 50 is positioned adjacent to the inferior end 65 of the basin 10. In this embodiment, the drain opening 50 may be positioned on a left side of the inferior end 65 of the basin 10 or on a right side of the inferior end 65 of the basin 10. In such embodiments a conduit 30 joined to the drain opening 50 may extend to the left or right, through a leg opening of a diaper worn by the patient. In another embodiment, the drain opening 50 may be positioned on a superior end 70 of the basin 10. In such embodiments a conduit 30 joined to the drain opening 50 may extend in the superior direction, through the waist of pants or a diaper worn by the patient.

In some embodiments, the basin 10 may include an absorbent body for retaining the urine within the bowl 40. For example, the interior of the basin 10 may include an absorbent body such as a sponge or cotton that can help retain the urine within the bowl 40 prior to draining. Such embodiments have the advantage of allowing the urine to be easily sampled by removing the absorbent material. The absorbent body can also be removed to analyze the urine, such as by measuring its quantity (especially where all of the urine is absorbed) or chemically analyzing it. In further embodiments of the device 500 the absorbent body may be positioned near the drain hole 50, to allow absorbed urine to be removed by suction periodically.

Figure 4B:
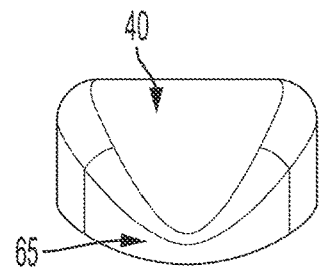
FIG. 4B is a view of an inferior end of the basin shown in FIG. 4A

FIG. 4B shows the inferior end 65 of the basin 10. In the illustrated embodiment, the bowl 40 is shaped and dimensioned such that the width (along the frontal axis) of the bowl 40 decreases from the superior end 70 to the inferior end 65. The decreasing width of the bowl 40, as illustrated in FIGS. 4A and 4B, provides for a shape that allows for a more secure fit on the patient by corresponding to the anatomical shape of the perineal region. In one embodiment, the width at the inferior end 65 up to about one-third of the width at the superior end 70. In another embodiment, the width at the inferior end 65 is up to about one-half of the width at the superior end 70.

Figure 4C:
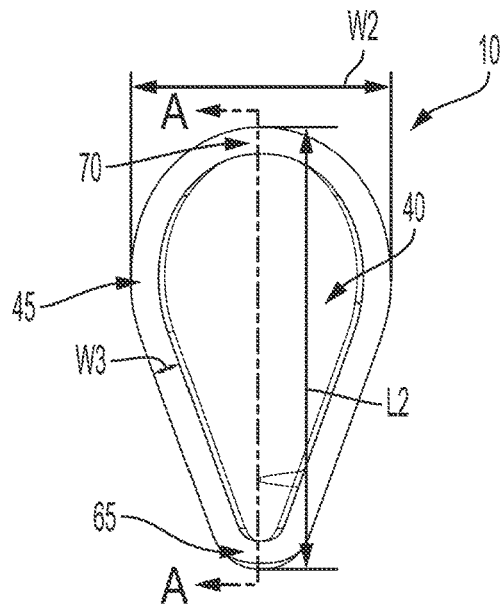
FIG. 4C is a top view of the basin shown in FIG. 4A.

FIG. 4C is a posterior view of the basin 10 shown in FIG. 4A. The basin 10 may have any volume sufficient for receiving and holding the urine excreted from the patient. In some embodiments, the basin 10 may have a width W2 along the frontal axis of at least about 0.60 inches. In another embodiment, the width W2 of the basin 10 is at least about 0.70 inches. In still another embodiment, the width W2 of the basin 10 is at least about 0.80 inches. In some embodiments of the basin W2 is 0.62-0.92 inches. In further embodiments of the basin W2 is 0.67-0.87 inches. In further embodiments of the basin W2 is 0.72-0.82 inches. In a specific embodiment of the basin W is 0.77 inches. Some embodiments of the basin 10 may have a length L2 along the vertical axis of at least about 1.10 inches. In another embodiment, the length L2 of the basin 10 is at least about 1.20 inches. In still another embodiment, the length L2 of the basin 10 is at least about 1.30 inches. In some embodiments of the basin L2 is 1.04-1.56 inches. In further embodiments of the basin L2 is 1.12-1.48 inches. In further embodiments of the basin L2 is 1.20-1.40 inches. In a specific embodiment of the basin L2 is 1.3 inches. The basin may have a length L2 greater than its width W2. In some embodiments of the basin L2 is 1.0-2.4 times W2. In further embodiments of the basin L2 is 1.4-2.0 times W2. In a specific embodiment L2 is 1.7 times W2.

The rim 45 of the bowl 40 is configured for attachment to the lip 15. The width of the rim 45 should be sufficiently sized for supporting the attachment of the lip 15. In one embodiment, the rim 45 has a width W3 of at least about 0.05 inches. In another embodiment, the width W3 of the rim 45 is at least about 0.07 inches. In still another embodiment, the width W3 of the rim 45 is at least about 0.08 inches. In still another embodiment, the width W3 of the rim 45 is at least about 0.10 inches. In some embodiments of the basin the rim 45 has a width W3 of 0.04-0.16 inches. In further embodiments of the basin the rim 45 has a width W3 of 0.06-0.12 inches. In a specific embodiment of the basin W3 is 0.08 inches.

Figure 4D:
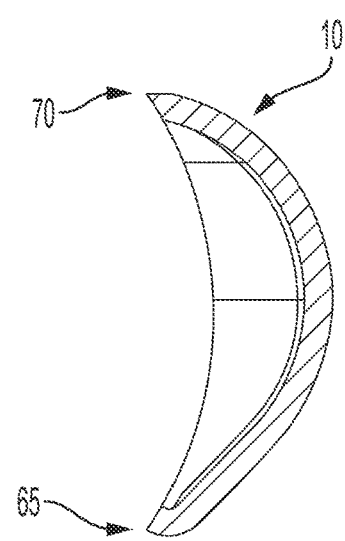
FIG. 4D is a cross sectional view of the basin shown in FIG. 4C taken along the line "A-A."

FIG. 4D is a cross sectional view of the basin 10 illustrated in FIG. 4C taken along the line "A-A." As shown in FIG. 4D, similar to the lip 15, the basin 10 has a profile that is contoured to define a curvature corresponding to the curvature of the patient's perineal region. However, the basin 10 may have any profile or shape that allows for a sufficient volume for collecting urine from the patient.

Figure 4E:
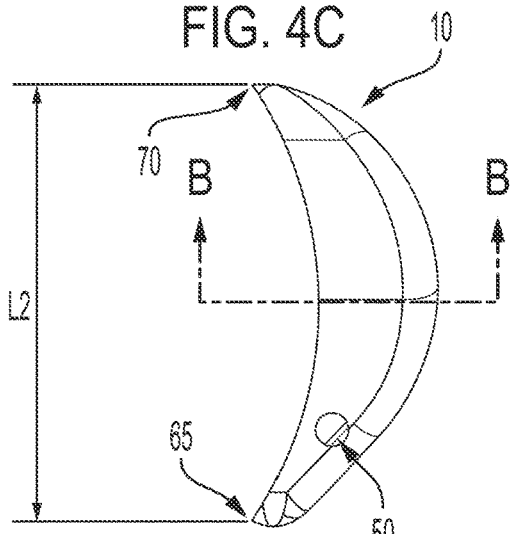
FIG. 4E is a side view of the basin shown in FIG. 4A.
Figure 4F:
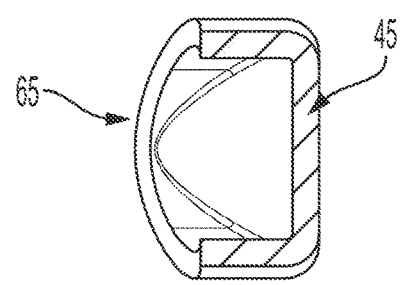
FIG. 4F is a cross sectional view of the basin shown in FIG. 4E taken along the line "B-B."

FIG. 4E is a side view of the basin 10 illustrated in FIG. 4A. FIG. 4F is a cross sectional view of the basin 10 illustrated in FIG. 4E taken along the line "B-B." As shown in FIG. 4E, the drain opening 50 is positioned adjacent to the inferior end 65 of the basin 10. The drain opening 50 may be any type of outlet capable of facilitating the draining of the urine collected in the basin 10. As will be described in more detail below, the drain opening 50 may also be configured for connecting the conduit 30. In some embodiments, the conduit 30 may be fluidly coupled to the drain opening 50 for draining the urine flowing through the drain opening 50 away from the urine collection device 500. Some embodiments of the conduit 30 are integral to the basin 10.

FIGS. 5A-5F show the ridge 25 according to an exemplary embodiment of the present disclosure. FIG. 5A is a perspective view of the ridge 25. FIG. 5B is a posterior view of the ridge 25. As discussed above, the illustrated embodiment of the ridge 25 is disposed on the lip 15 and is positioned and dimensioned to extend between the patient's labia to create a waterproof fit during use. For example, the ridge 25 can function to prevent leakage of urine from the inferior end 65 of the basin 10 during use.

As illustrated in FIGS. 5A and 5B, the ridge 25 comprises an anterior edge 75. In one embodiment, the anterior edge 75 defines a "V" shape having a curved apex 90 and two side stems: a first stem 95 and a second stem 100. In some embodiments, the first stem 95 and the second stem 100 may be positioned at an angle sufficient to extend between the patient's labia. In one embodiment, the first stem 95 and the second stem 100 are positioned about 25 degrees to about 65 degrees from each other. In another embodiment, the first stem 95 and the second stem 100 are positioned about 30 degrees to about 60 degrees from each other. In still another embodiment, the first stem 95 and the second stem 100 are positioned about 35 degrees to about 55 degrees from each other. In still other embodiments, the first stem 95 and the second stem 100 are positioned about 40 degrees to about 50 degrees from each other. In a specific embodiment of the ridge 25 the angle between the first stem 95 and the second stem 100 is about 44 degrees.

FIG. 5C shows an inferior view of the ridge 25. As illustrated in FIG. 5C, the ridge 25 has a vertical height H1 defined between the anterior edge 75 and a posterior edge 80 along the sagittal axis. In this embodiment, the vertical height H1 between the anterior edge 75 and the posterior side 80 should be sufficiently sized to prevent urine from leaking out of the inferior end 65 of the basin 10. In one embodiment, H1 is at least about 0.10 inches. In another embodiment, H1 is at least about 0.15 inches. In still another embodiment, the vertical height H1 is at least about 0.20 inches. In yet another embodiment, the vertical height H1 is at least about 0.25 inches. In further embodiments of the ridge H1 is 0.10-0.42 inches. In still further embodiments of the ridge H1 is 0.15-0.32 inches. In still further embodiments of the ridge H1 is 0.18-0.24 inches. In a specific embodiment of the ridge H1 is 0.21 inches.

FIG. 5D is a cross sectional view of the ridge 25 illustrated in FIG. 5C taken along the line "A-A." The cross sectional view shown in FIG. 5D illustrates the sagittal cross section of the first stem 95. As can be seen, the posterior edge 80 of the first side stem 95 forms a curvature corresponding to the curvature of the contact surface 20 of the lip 15. This curvature helps create a watertight seal when the ridge 25 is disposed on the lip 15.

FIG. 5E is a side view of the ridge 25 illustrated in FIGS. 5A and 5B. As illustrated in FIG. 5E, the curved apex 90 has a height H2. In one embodiment, the height H2 of the curved apex 90 is less than the height H1 between the anterior edge 75 and the posterior side 80. As shown in FIG. 5E, the shape of the ridge 25 extending from the posterior edge 80 to the curved apex 90 may be formed at an angle. In one embodiment, the shape of the ridge 25 extending from the posterior edge 80 to the curved apex 90 may be formed at an angle ranging from about 100 degrees to about 140 degrees. In another embodiment, the shape of the ridge 25 extending from the posterior edge 80 to the curved apex 90 may be formed at an angle ranging from about 110 degrees to about 130 degrees. In still another embodiment, the shape of the ridge 25 extending from the posterior edge 80 to the curved apex 90 may be formed at an angle ranging from about 115 degrees to about 125 degrees. In a specific embodiment of the ridge 25 the angle is about 120 degrees.

FIG. 5F is a cross sectional view of the ridge 25 illustrated in FIG. 5E taken along the line "B-B." The ridge 25 may be sized and dimensioned to fit on the lip 15 such that the width of the ridge 25 does not exceed the width of the lip 15. In one embodiment, the ridge 25 has a width W4 of at least about 0.50 inches. In another embodiment, the ridge 25 has a width W4 of at least about 0.55 inches. In still another embodiment, the ridge 25 has a width W4 of at least about 0.60 inches.

Figure 6A:
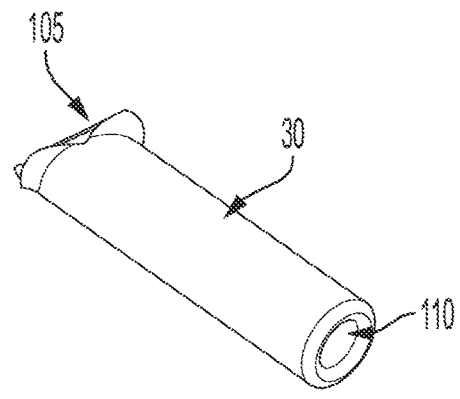
FIG. 6A is a front perspective view of a conduit of the urine collection device according to an exemplary embodiment of the present disclosure.
Figure 6B:
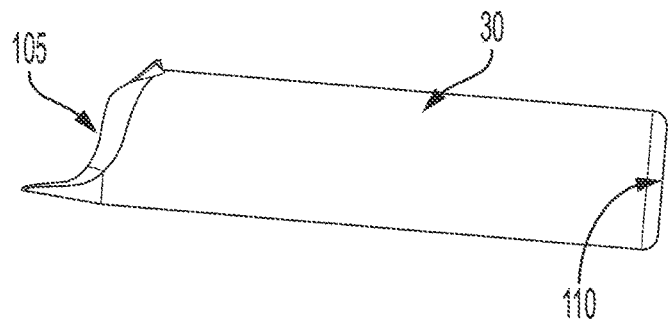
FIG. 6B is a side view of the conduit shown in FIG. 6A.

FIGS. 6A-6D illustrate the conduit 30 according to an exemplary embodiment of the present disclosure. FIGS. 6A and 6B show a front perspective view and a side view, respectively, of the conduit 30. As shown in FIGS. 6A and 6B, the conduit 30 is an elongated channel capable of allowing for urine or other liquids to pass through. The conduit 30 may be any type of channel configured for the passage of liquids, such as a port, tube, or pipe. In the illustrated embodiment, the conduit 30 has a first end 105 configured to be fluidly attached to the drain opening 50 and a second end 110 configured to be fluidly attached to a collection container for disposal of the drained urine. Each of the first end 105 and the second end 110 may be attached to the drain opening 50 and collection container, respectively, by any suitable connection means. For instance, each of the first end 105 and the second end 110 may include a threaded fitting that is configured for coupling to a corresponding threaded fitting. In other embodiments, each of the first end 105 and the second end 110 may be secured to the drain opening 50 or the collection container using screws, pins, fasteners, or rivets. In an alternative embodiment of the device 500 the conduit 30 is formed integrally with the basin 110 at an integrally formed drain opening 50.

Figure 6C:
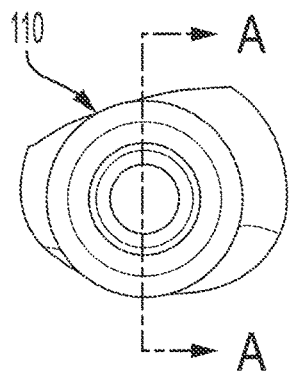
FIG. 6C is a front view of the conduit shown in FIG. 6A.
Figure 6D:
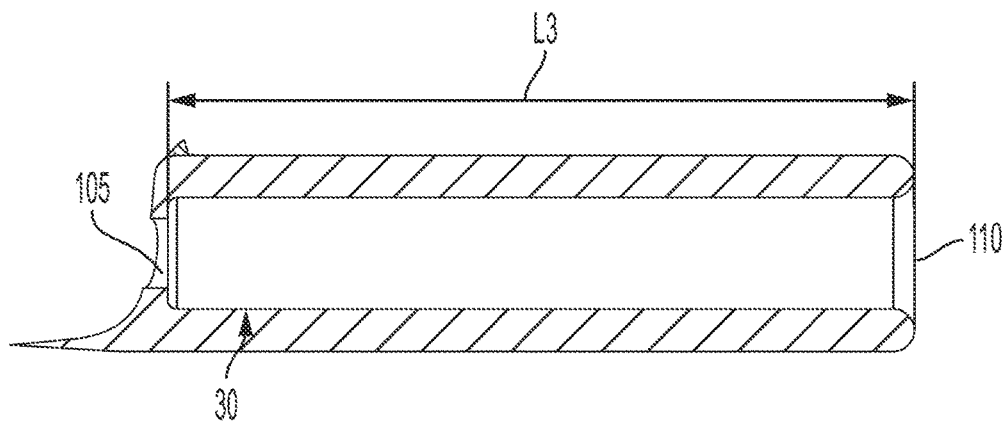
FIG. 6D is a cross sectional view of the conduit shown in FIG. 6C taken along the line "A-A."

FIG. 6C is a front view of the conduit 30 and FIG. 6D is a cross sectional view of the conduit 30 illustrated in FIG. 6C taken along the line "A-A." As shown in FIGS. 6C and 6D, the conduit 30 has an inner hollow channel allowing for the urine and other liquids to pass through and into an external collection container. The conduit 30 may have any suitable dimensions for allowing urine to drain from the basin 10 to the collection container. In one embodiment, the conduit 30 has a length L3 of at least about 0.70 inches. In another embodiment, the conduit 30 has a length L3 of at least about 0.80 inches. In still another embodiment, the conduit 30 has a length L3 of at least about 0.90 inches. In yet another embodiment, the conduit 30 has a length L3 of at least about 1.0 inch.

In some embodiments, the conduit 30 may incorporate a flowmeter, for instance, an electronic flowmeter, configured for measuring a rate of flow of the urine into the collection container. Alternatively a mechanical or optical flowmeter can be used, or other flowmeters suitable for measuring the rate of flow of urine. In another embodiment, the conduit 30 may include an indicator configured for determining whether the patient has an infection or injury based on the levels of certain substances in the urine, such as proteins, ketones, hemoglobin, nitrites, and harmful pathogens. For example, the conduit 30 or basin may incorporate a test strip urinalysis that can check the appearance, concentration, and content of urine and detect a wide range of medical disorders, such as urinary tract infections (UTI's), kidney disease and diabetes. A specific embodiment of the test strip is a standard urine test strip, with colorimetric assays for one or more of leukocytes, nitrates, urobilinogen, protein, blood, pH, specific gravity, ketone, bilirubin, and glucose.

Figure 7A:
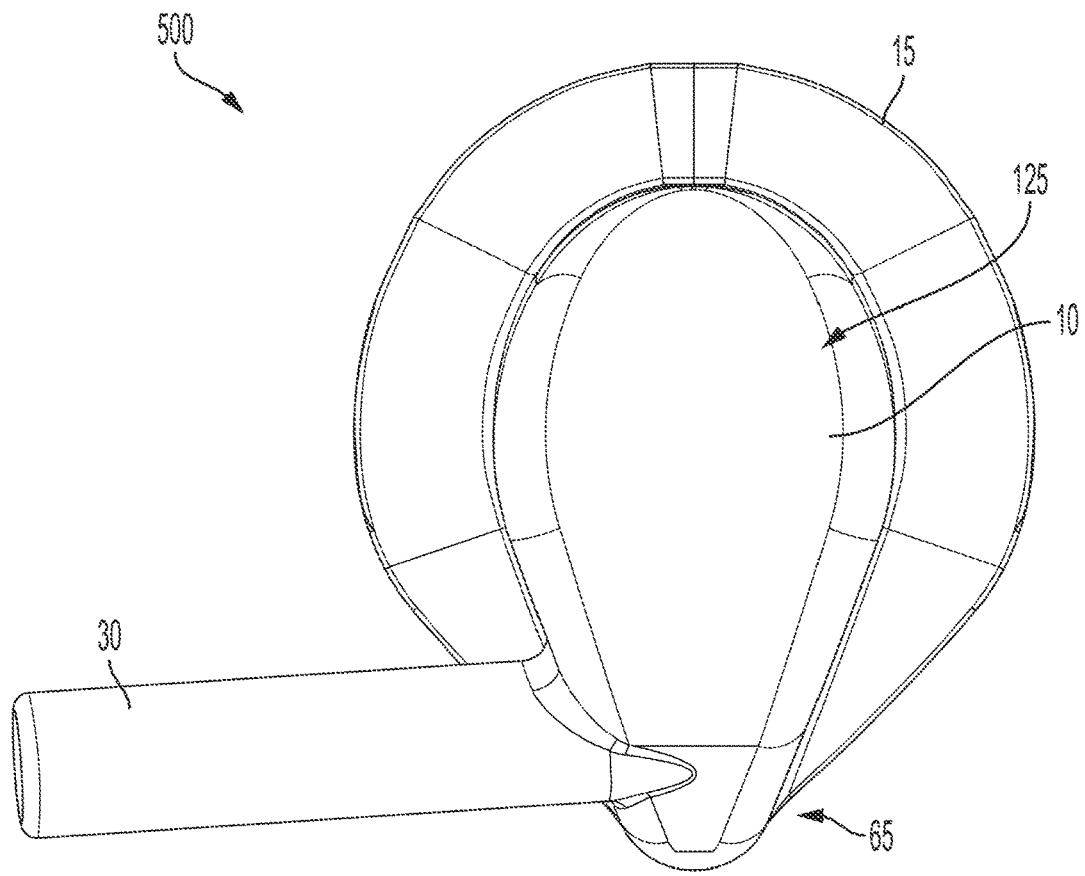
FIG. 7A is a rear perspective view of the urine collective device shown in FIG. 1A.
Figure 7B:
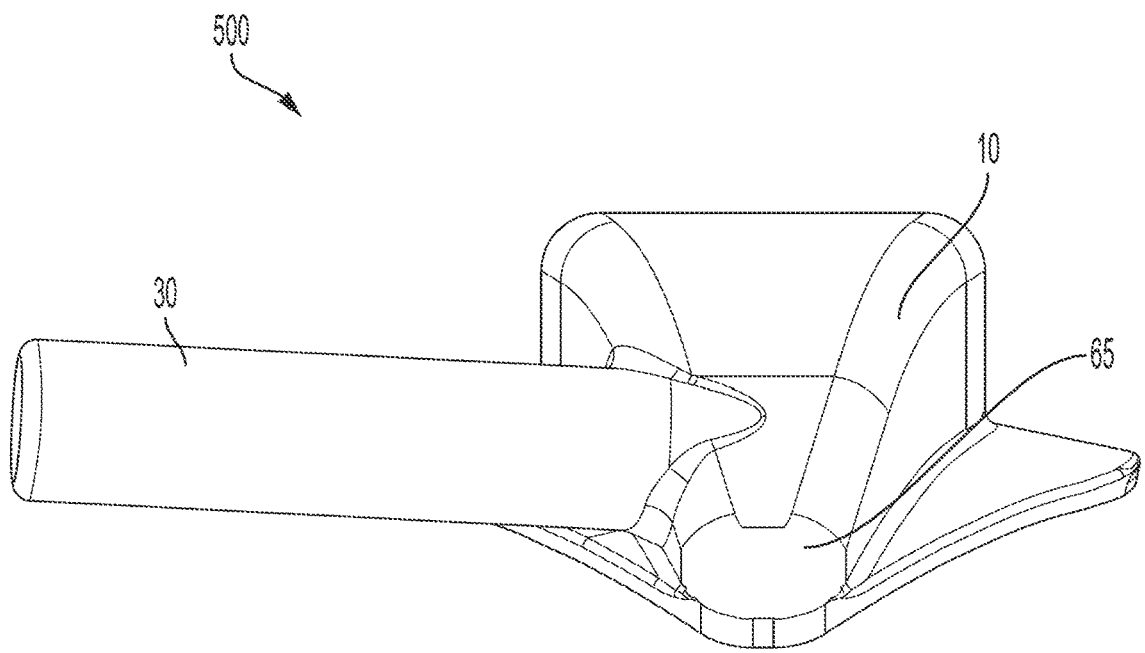
FIG. 7B is another rear view of the urine collection device shown in FIG. 1A.

FIGS. 7A and 7B show rear views of the urine collection device 500 according to an exemplary embodiment. As shown in FIGS. 7A and 7B, the conduit 30 may be fluidly coupled to the basin 10 at the drain opening 50 on an anterior side 125 of the device 500. The conduit 30 may be positioned to facilitate draining urine away from the patient's body, thus minimizing the amount of time that urine is in contact with the patient's skin. Such drainage may be accomplished by gravity in some embodiments of the device. In alternative embodiments of the device the drainage may be accomplished by use of suction or negative pressure. For instance, as shown in FIGS. 7A and 7B, the conduit 30 may be positioned at an angle relative to the longitudinal axis of the basin 10 to facilitate draining urine away from the patient's body. In one embodiment, the conduit 30 may be fluidly coupled to the basin 10 at an angle of at least about 80 degrees. In another embodiment, the conduit 30 may be fluidly coupled to the basin 10 at an angle of at least about 85 degrees. In still another embodiment, the conduit 30 may be fluidly coupled to the basin 10 at an angle of at least about 90 degrees. In yet another embodiment, the conduit may be fluidly coupled to the basin 10 at an angle of at least about 95 degrees.

In some embodiments, the positioning of the conduit 30, as shown in FIGS. 7A and 7B, allows for the urine collection device 500 to be worn with an undergarment, such as a diaper. For instance, when the drain opening 50 is positioned adjacent to the inferior end 65 of the basin 10 on a right or left side (as illustrated), the conduit 30 may extend outside the leg of a diaper. In another embodiment, when the drain opening 50 is positioned on the superior end 70 of the basin 10, the conduit 30 may extend upwardly out of the top of the diaper.

Figure 8A:
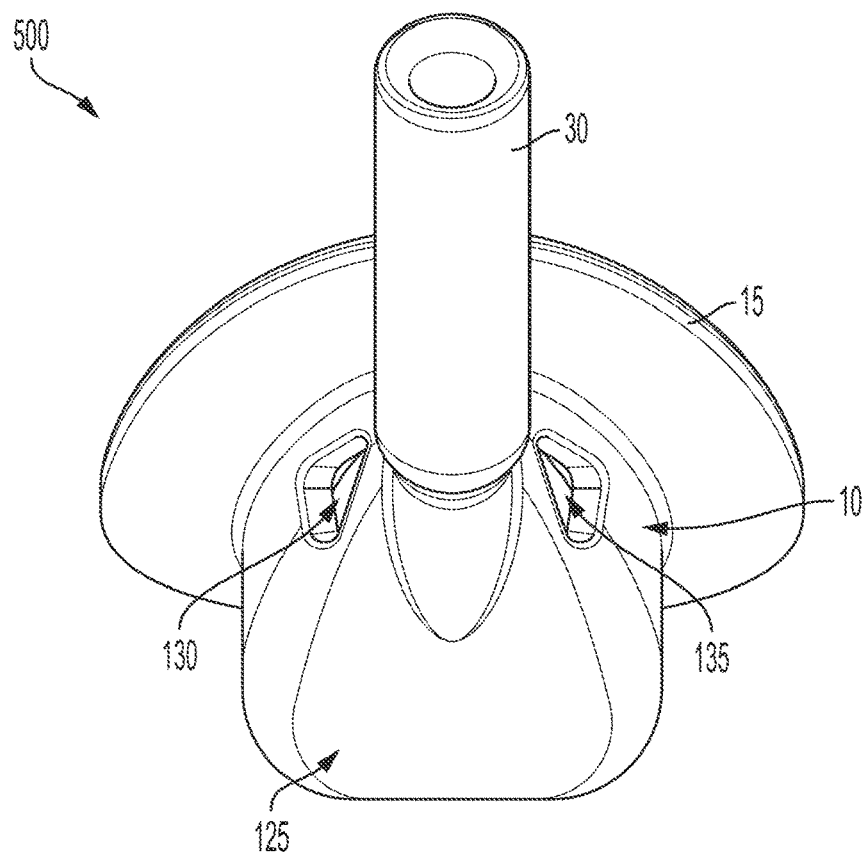
FIG. 8A is a rear perspective view of a urine collection device according to another embodiment of the present disclosure, configured for suction drainage.
Figure 8B:
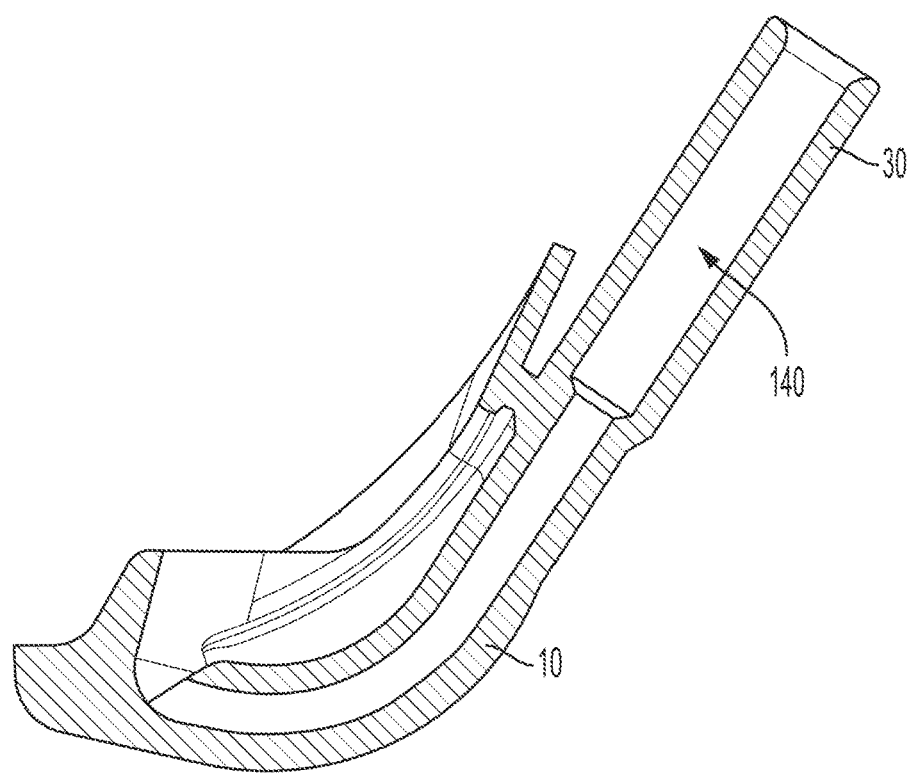
FIG. 8B is a cross sectional view of the urine collection device shown in FIG. 8B.

FIGS. 8A and 8B show the urine collection device 500 according to another embodiment of the present disclosure, where the urine collection device is configured for suction drainage. In an embodiment of the device 500 shown in FIGS. 8A and 8B, the drain opening 50 is located at the inferior end 85 of the device 500, and the conduit 30 runs to the superior end 115 of the device 500 where it can emerge from the waist of a diaper or other garments. In the embodiment of the device 500 shown in FIG. 8A, a first vent 130 and a second vent 135 are located in the basin 10, proximate to the superior end 115, which allow suctioning of urine through the conduit 30 while equalizing the pressure in the basin 10. As illustrated in FIG. 8B, the conduit 30 may also include an inner tube 140 to allow negative pressure to suction out the urine from the superior end 70 of the basin 10.

Figure 10:
FIG. 10 is a cross-sectional view of an embodiment of the device when in place on the perineal region of the patient.

FIGS. 9 and 10 show the urine collection device 500 when in place on a patient 200. As shown in FIGS. 9 and 10, the urine collection device 500 is configured to be worn externally on the patient 200. The urine collection device 500 is positioned to surround the perineal region of the patient 200 such that urine excreted by the patient 200 can be collected in the basin 10 of the urine collection device 500.

The urine collection device 500 may be formed of any biologically compatible material. Some embodiments of a suitable material may have one or more characteristics of being non-toxic, hypoallergenic, and non-irritant. In one embodiment, the urine collection device 500 is formed of a soft, flexible polymeric material. Forming the urine collection device 500 of a soft, flexible polymeric material allows for the urine collection device 500 to conform to the patient's body and provides for a more comfortable fit during use. Examples of suitable polymeric materials include, but are not limited to, silicone, rubber, thermoplastic elastomers, or any combination thereof. A specific embodiment of the polymeric material is medical-healthcare grade silicone, such as class VI medical-healthcare grade silicone. Another specific embodiment of the polymeric material is an elastomeric 3D printing ink, such as TANGO BLACK PLUS FLX980 or VERO WHITE PLUS RGD835 (distributed by StrataSys Ltd., Eden Prairie, MN, USA). A further embodiment of the polymeric material is VERSALLO HEALTHCARE SERIES, especially those that comply with ISO 10993-1:2018 (2018) (Avient Corporation, Avon Lake, OH, USA).

The dimensions of the urine collection device 500 described herein are exemplary dimensions. As will be readily apparent to one of ordinary skill in the art, the urine collection device 500 may be formed in multiple different sizes to allow for a more custom fit to each patient based on body characteristics, such as height and weight. In some embodiments, the urine collection device 500 may be adapted for an adult. In this embodiment, the dimensions of the urine collection device 500 may be increased by about three times, preferably about four times, and more preferably about five times.

Systems for collecting and measuring urine excreted by a patient are also provided herein. In one embodiment, the system includes the urine collection device 500 described herein and any of the adhesives described above disposed on the lip 15. In further embodiments, the system may further include an external collection container in fluid communication with the urine collection device 500 described herein. For instance, the collection container may be fluidly coupled to the urine collection device 500 using the conduit 30. The collection container can be configured to quantify the urine excreted by the patient. Examples of suitable collection containers for quantifying the urine output include, but are not limited to, a collection tube, a urine collection bag, a suction canister, a specimen container, a specimen trap, or any combination thereof. The container may be configured to quantify the urine in various ways, such as using marked volumetric gradations on the container.

In some embodiments, the systems provided herein may also include a suction device configured to suction the urine from the urine collection device to the collection container. For instance, the urine collection device disclosed herein may be adapted for use with a manual or powered suction device to facilitate removing excreted urine by applying negative pressure to the urine collection device. The use of the suction device may be particularly advantageous for draining the urine when the drain opening 50 is located on the superior end 70 of the basin 10. The suction device may be coupled with the conduit 30 for transporting the drained urine into the collection container. In one embodiment, the suction device may be a manual device, such as a squeeze pump or a bellows pump. In another embodiment, the suction device may be a peristaltic pump. In still another embodiment, the suction device may be a wall suction.

Methods of Use

The urine collection device 500 described herein can be used, for instance, to collect urine and measure urine output of a female patient. The method may include attaching the urine collection device 500 described herein to the perineal region of the patient, for instance, by using an adhesive disposed on the lip 15, and collecting urine excreted by the patient in the urine collection device 500. In another embodiment, the method may be used for measuring urine excreted by a patient. Measuring the urine may comprise draining the urine into a collection container, and quantifying the urine by weight or volume.

In further embodiments, the methods of the present disclosure may include quantifying the urine by measuring a rate of flow of the urine into the collection container. For instance, the rate of flow of the urine into the collection container may be measured with a flowmeter. Suitable examples of flowmeters include electronic, mechanical, and optical flowmeters. In still other embodiments, the methods of the present disclosure may include a step for measuring levels of certain substances in the urine, such as proteins, ketones, hemoglobin, nitrites, and harmful pathogens, and detecting an infection or injury, such as urinary tract infections (UTIs), kidney disease, and diabetes, based on the measured levels. For instance, the measuring step may be performed using a test strip urinalysis.

In some embodiments, the methods may include prepping the perineal area (for example, the region around the urethra) to facilitate forming a liquid tight seal between the adhesive and the patient's skin. Preparing the patient's body may include cleaning the perineal area and the area around the urethra using water, soap, and/or alcohol and optionally drying the cleaned area.

In other embodiments, the methods may further include providing negative pressure to assist in draining the urine into the collection container. The use of negative pressure may be advantageous for those patients who are lying down or are not mobile. As noted above, the use of negative pressure is also useful for draining the urine when the drain opening 50 is positioned on the superior end 70 of the basin 10. For instance, the urine may be drained into the collection container using suctioning, as described above. In another embodiment, the urine may be drained into the collection container by pumping the urine into the collection container. In still other embodiments, gravity may be sufficient for draining the urine into the collection container.

Exemplary Embodiments

In addition to anything described above or currently claimed, it is specifically contemplated that any of the following embodiments may be claimed:

Embodiment 1. A urine collection device, comprising: a basin configured to fit a perineal region of a female human subject and to receive urine; a lip attached to the basin and having a contact surface for attachment to the perineal region; a ridge extending away from the interior of the basin and disposed along an inferior portion of the device to prevent leakage of urine from the basin; and a drain opening in the basin for draining the urine.

Embodiment 2. A urine collection device, comprising: a basin configured to fit a perineal region of a female human subject and to receive urine; a lip attached to the basin and having a surface area sufficient to adhere the device to the female human subject using an adhesive; a ridge on an inferior end of the basin to prevent leakage of urine from the basin; and a drain opening in the basin for draining the urine.

Embodiment 3. A urine collection device for use by a female pediatric subject, the device comprising: a basin having a bowl and a rim, the bowl dimensioned to cover the subject's urethra and the rim dimensioned to contact a region surrounding the urethra; a lip extending radially from the rim of the basin and configured to contact the subject's abdomen or mons pubis; a ridge extending away from the bowl of the basin on an inferior side of the basins, the ridge configured to create a seal by extending between the subject's labia; and a drain opening positioned on the basin for draining urine from the basin.

Embodiment 4. The urine collection device of any one of the embodiments above, for use by a female pediatric subject, wherein the human pediatric subject is a neonate, infant, or a toddler.

Embodiment 5. The urine collection device of any one of the embodiments above, wherein the basin is dimensioned to extend between the subject's legs to a distance at least exceeding the urethra.

Embodiment 6. The urine collection device of any one of the embodiments above, wherein the basin is dimensioned to extend vertically from the abdomen superior to the urethra between the subject's legs at least to the perineum.

Embodiment 7. The urine collection device of any one of the embodiments above, wherein the lip is contoured to define a curved surface corresponding to a curvature of the subject's perineal region.

Embodiment 8. The urine collection device of any one of the embodiments above, wherein the lip is contoured to define a concavity on the side opposite the basin.

Embodiment 9. The urine collection device of any one of the embodiments above, wherein the lip has a profile in sagittal cross-section of an arc of about 100-135°.

Embodiment 10. The urine collection device of any one of the embodiments above, wherein an adhesive is disposed on the lip.

Embodiment 11. The urine collection device of any one of the embodiments above, wherein an adhesive is disposed on at least one of an anterior surface of the lip and a posterior surface of the lip.

Embodiment 12. The urine collection device of any one of the embodiments above, wherein an adhesive is disposed on the lip and wherein the adhesive is a medical grade pressure sensitive adhesive.

Embodiment 13. The urine collection device of any one of the embodiments above, wherein an adhesive is disposed on the lip and wherein the adhesive comprises medical grade tape.

Embodiment 14. The urine collection device of any one of the embodiments above, wherein the lip has a surface defined by an inner perimeter and an outer perimeter and the width between the inner and outer perimeter is at least about 0.1 inches.

Embodiment 15. The urine collection device of any one of the embodiments above, wherein the lip has a surface defined by an inner perimeter and an outer perimeter and wherein the inner perimeter of the lip defines an opening having a width of at least about 0.50 inches along a frontal axis.

Embodiment 16. The urine collection device of any one of the embodiments above, wherein the lip has a surface defined by an inner perimeter and an outer perimeter and wherein the inner perimeter of the lip defines an opening having a length of at least about 0.80 inches along a vertical axis.

Embodiment 17. The urine collection device of any one of the embodiments above, wherein the lip has a surface defined by an inner perimeter and an outer perimeter, the inner perimeter of the lip defines an opening having a length along a vertical axis and a width along a frontal axis, and the length is about twice the width.

Embodiment 18. The urine collection device of any one of the embodiments above, wherein the drain opening is positioned on the superior end of the basin.

Embodiment 19. The urine collection device of any one of the embodiments above, wherein the drain opening is positioned adjacent to the inferior end of the basin on a right or left side.

Embodiment 20. The urine collection device of any one of the embodiments above, further comprising a conduit fluidly coupled to the drain opening for draining urine from the basin.

Embodiment 21. The urine collection device of any one of the embodiments above, wherein the device is made from a hypoallergenic material.

Embodiment 22. The urine collection device of any one of the embodiments above, wherein the device is made from a polymeric material comprising silicone, rubber, thermoplastic elastomers, or combinations thereof.

Embodiment 23. The urine collection device of any one of the embodiments above, wherein the ridge is dimensioned to extend between the subject's labia.

Embodiment 24. The urine collection device of any one of the embodiments above, wherein the ridge is dimensioned to extend between the subject's labia and create a waterproof fit.

Embodiment 25. The urine collection device of any one of the embodiments above, wherein the ridge comprises an anterior edge forming a "V" with a curved apex and with two stems at about 25-65° from each other.

Embodiment 26. A method of collecting urine excreted by an infant, comprising: attaching the urine collection device of any one of the embodiments above to a perineal region of the infant, wherein an adhesive is on the lip; and collecting urine excreted by the infant in the urine collection device.

Embodiment 27. A method of measuring urine excreted by an infant, comprising: attaching the urine collection device of any one of the embodiments above to a perineal region of the infant; collecting urine excreted by the infant in the urine collection device; and quantifying the urine.

Embodiment 28. The method of any one of the embodiments above, further comprising draining the urine into a collection container.

Embodiment 29. The method of any one of the embodiments above, wherein the draining step comprises providing negative pressure to assist in draining the urine into the collection container.

Embodiment 30. The method of any one of the embodiments above, wherein the draining step comprises providing negative pressure to assist in draining the urine into the collection container, and wherein the drain opening is located at a superior end of the basin.

Embodiment 31. The method of any one of the embodiments above, wherein the draining step comprises suctioning the urine into the collection container.

Embodiment 32. The method of any one of the embodiments above, wherein the draining step comprises pumping the urine into the collection container.

Embodiment 33. The method of any one of the embodiments above, wherein the attaching step consists of attaching the urine collection device to the infant using an adhesive.

Embodiment 34. The method of any one of the embodiments above, comprising quantifying the urine by measuring a rate of flow of the urine into the collection container.

Embodiment 35. The method of any one of the embodiments above, comprising quantifying the urine by measuring a rate of flow of the urine into the collection container with an electronic flowmeter.

Embodiment 36. The method of any one of the embodiments above, comprising detecting an analyte in the urine using an assay placed in the basin.

Embodiment 37. The method of any one of the embodiments above, comprising absorbing a volume of the urine in an absorbent body located in the basin; and quantifying the urine in the absorbent body.

Embodiment 38. The method of any one of the embodiments above, comprising absorbing a volume of the urine in an absorbent body located in the basin; and removing the volume of urine by suction.

Embodiment 39. A system for collecting and measuring urine excreted by a pediatric female subject, comprising: the urine collection device of any one of the embodiments above; and an adhesive on the lip of the urine collection device.

Embodiment 40. The system of any one of the embodiments above, comprising a collection container in fluid communication with the urine collection device.

Embodiment 41. The system of any one of the embodiments above, comprising a collection container in fluid communication with the urine collection device configured to quantify the urine excreted by the subject.

Embodiment 42. The system of any one of the embodiment above, wherein the collection container is fluidly coupled to a urine collection device using a conduit.

Embodiment 43. The system of any one of the embodiments above, comprising a suction device configured to suction the urine from the urine collection device to the collection container.

Embodiment 44. The system of any one of the embodiments above, comprising an indicator configured for detecting an injury or infection based on levels of substances in the urine.

Embodiment 45. The system of any one of the embodiments above, comprising an absorbent body in the basin capable of absorbing a volume of urine.

REFERENCES

The following references are provided to aid in the understanding of the disclosure above. No admission is made that any reference below meets the legal definition of "prior art" in any jurisdiction, or that any reference is relevant or irrelevant to the patentability of anything disclosed above.

1. Kellum J A, Lameire N, for the KAKIGWG. Diagnosis, evaluation, and management of acute kidney injury: a KDIGO summary (Part 1). Crit Care. 2013; 17(1):204.

2. Sutherland S M, Zappitelli M, Alexander S R, et al. Fluid overload and mortality in children receiving continuous renal replacement therapy: the prospective pediatric continuous renal replacement therapy registry. *American journal of kidney diseases: the official journal of the National Kidney Foundation.* 2010; 55(2):316-325.

3. Mariano F, Melia A, Vincenti M, Biancone L. Furosemide as a functional marker of acute kidney injury in ICU patients: a new role for an old drug. *J Nephrol.* 2019.

4. Rewa O G, Bagshaw S M, Wang X, et al. The furosemide stress test for prediction of worsening acute kidney injury in critically ill patients: A multicenter, prospective, observational study. *J Crit Care.* 2019; 52:109-114.

5. Basu R K, Chawla L S, Wheeler D S, Goldstein S L. Renal angina: an emerging paradigm to identify children at risk for acute kidney injury. *Pediatric nephrology* (Berlin, Germany). 2012; 27(7):1067-1078.

6. Diamond H, Meisel A. Influence of volume expansion, serum sodium, and fractional excretion of sodium on urate excretion. *Pflugers Arch.* 1975; 356(1):47-57.

7. Endre Z H, Kellum J A, Di Somma S, et al. Differential diagnosis of AKI in clinical practice by functional and damage biomarkers: workgroup statements from the tenth Acute Dialysis Quality Initiative Consensus Conference. *Contrib Nephrol.* 2013; 182:30-44.

8. Ostermann M, Philips B J, Forni L G. Clinical review: Biomarkers of acute kidney injury: where are we now? *Crit Care.* 2012; 16(5):233.

9. Stanski N, Menon S, Goldstein S L, Basu R K. Integration of urinary neutrophil gelatinase-associated lipocalin with serum creatinine delineates acute kidney injury phenotypes in critically ill children. *J Crit Care.* 2019; 53:1-7.

10. Kaddourah A, Basu R K, Goldstein S L, Sutherland S M, Assessment of Worldwide Acute Kidney Injury RAaEI. Oliguria and Acute Kidney Injury in Critically Ill Children: Implications for Diagnosis and Outcomes. *Pediatric critical care medicine: a journal of the Society of Critical Care Medicine and the World Federation of Pediatric Intensive and Critical Care Societies.* 2019; 20(4):332-339.

11. Siegel B I, Figueroa J, Stockwell J A. Impact of a Daily PICU Rounding Checklist on Urinary Catheter Utilization and Infection. *Pediatr Qual Saf* 2018; 3(3):e078. Conclusions It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description and accompanying drawings illustrate and describe certain processes, machines, manufactures, and compositions of matter, some of which embody the invention(s). Such descriptions or illustrations are not intended to limit the scope of what can be claimed, and are provided as aids in understanding the claims, enabling the making and use of what is claimed, and teaching the best mode of use of the invention(s). If this description and accompanying drawings are interpreted to disclose only a certain embodiment or embodiments, it shall not be construed to limit what can be claimed to that embodiment or embodiments. Any examples or embodiments of the invention described herein are not intended to indicate that what is claimed must be coextensive with such examples or embodiments. Where it is stated that the invention(s) or embodiments thereof achieve one or more objectives, it is not intended to limit what can be claimed to versions capable of achieving all such objectives. Any statements in this description criticizing the prior art are not intended to limit what is claimed to exclude any aspects of the prior art.

Additionally, the disclosure shows and describes certain embodiments of the processes, machines, manufactures, compositions of matter, and other teachings disclosed, but it is to be understood that the teachings of the present disclosure are capable of use in various other combinations, modifications, and environments and is capable of changes or modifications within the scope of the teachings as expressed herein.

Any section headings herein are provided only for consistency with the suggestions of 37 C.F.R. § 1.77 or otherwise to provide organizational queues. These headings shall not limit or characterize the invention(s) set forth herein.

What is claimed is:

1. A urine collection device, comprising:
   a. a basin configured to fit a perineal region of a female human subject and to receive urine, the basin having an inferior end and a superior end;
   b. a lip attached to the basin and having a contact surface for attachment to the perineal region, contoured to define a curved surface corresponding to a curvature of the subject's perineal region, and having an inferior end at the inferior end of the basin;
   c. a ridge, comprising: a posterior/inferior edge, an anterior/superior edge forming a "V" with a curved apex when seen from above, the ridge being disposed along only an inferior portion of the device and absent on the superior portion of the device to prevent leakage of urine from the basin, wherein the curved apex protrudes dorsally away from the interior of the basin, and wherein the ridge is configured to extend into the vestibule of the vaginal opening of the subject; and
   d. a drain opening in the basin for draining the urine.

2. The urine collection device of claim 1, wherein the female human subject is a neonate, infant, child, or toddler.

3. The urine collection device of claim 1, wherein the basin is dimensioned to extend between the subject's legs to a distance at least exceeding the urethra.

4. The urine collection device of claim 1, wherein the basin is dimensioned to extend vertically from the abdomen superior to the urethra between the subject's legs at least to the perineum.

5. The urine collection device of claim 1, wherein the lip is contoured to define a curved surface corresponding to a curvature of the subject's perineal region.

6. The urine collection device of claim 1, wherein the lip is contoured to define a concavity on the side opposite the basin.

7. The urine collection device of claim 1, wherein the lip has a profile in sagittal cross-section of an arc of about 100-135°.

8. The urine collection device of claim 1, wherein the lip has a surface defined by an inner perimeter and an outer perimeter, the inner perimeter of the lip defines an opening having a length along a vertical axis and a width along a frontal axis, and the length is about twice the width.

9. The urine collection device of claim 1, wherein the drain opening is positioned on the superior end of the basin.

10. The urine collection device of claim 1, wherein the drain opening is positioned adjacent to the inferior end of the basin on a right or left side.

11. The urine collection device of claim 1, further comprising a conduit fluidly coupled to the drain opening for draining urine from the basin.

12. The urine collection device of claim 1, wherein the "V" formed by the anterior/superior edge of the ridge comprises two stems at about 25-65° from each other.

13. A method of collecting urine excreted by an infant, comprising:
   a. attaching the urine collection device of claim 1 to a perineal region of the infant, wherein an adhesive is on the lip; and b. collecting urine excreted by the infant in the urine collection device.

14. A method of measuring urine excreted by an infant, comprising;
   a. attaching the urine collection device of claim 1 to a perineal region of the infant; and
   b. collecting urine excreted by the infant in the urine collection device; and c. quantifying the urine.

15. A system for collecting and measuring urine excreted by a pediatric female subject, comprising:
   a. the urine collection device of claim 1; and
   b. an adhesive on the lip of the urine collection device.

16. The urine collection device of claim 1, comprising a tube and a collection container connected to the drain opening to receive urine.

17. The urine collection device of claim 1, wherein the ridge extends from the posterior/inferior edge of the device to the curved apex at an angle of over 90°.

18. The urine collection device of claim 1, wherein the ridge extends from the posterior/inferior edge of the device in an anterior/superior direction to the curved apex at an angle of 90-120°.

19. The urine collection device of claim 1, wherein the ridge extends from the posterior/inferior edge of the device in an anterior/superior direction to the curved apex at an angle of 100-140°.

20. The urine collection device of claim 1, wherein an inferior end of the ridge is anterior/superior to the inferior end of the lip to accommodate space for the lip to contact the perineal area of the female subject.

21. The urine collection device of claim 1, wherein the curved apex extends from the posterior/inferior edge of the ridge anteriorly/superior to the curved apex at an angle of over 90°.

22. The urine collection device of claim 1, wherein the device is configured to form a seal to prevent urine from leaking posteriorly/inferiorly.

23. The urine collection device of claim 1, wherein the ridge is configured to channel urine into the basin.

24. The urine collection device of claim 1, wherein the ridge is configured to prevent stool contamination into the basin.

25. The urine collection device of claim 1, wherein when the device is placed on the subject, the curved apex is dorsal to the subject's vestibule, superior to the subject's posterior fourchette, inferior to the subject's urethra, and ventral to the subject's urethra.

26. A urine collection device, comprising:
   a. a basin configured to fit a perineal region of a female human subject and to receive urine, the basin having an inferior end and a superior end;
   b. a lip attached to the basin and having a surface area sufficient to adhere the device to the female human subject using an adhesive, contoured to define a curved surface corresponding to a curvature of the subject's perineal region, and having an inferior end at the inferior end of the basin;
   c. a ridge on only an inferior end of the basin and absent on the superior end of the basin to prevent leakage of urine from the basin, said ridge comprising an anterior/superior edge forming a "V" with a curved apex when seen from above, wherein the curved apex protrudes dorsally away from the interior of the basin, and wherein the ridge is configured to extend into the vestibule of the vaginal opening of the subject; and
   d. a drain opening in the basin for draining the urine.

27. A urine collection device for use by a female pediatric subject, the device comprising:
   a. a basin having a bowl and a rim, the bowl dimensioned to cover the subject's urethra and the rim dimensioned to contact a region surrounding the urethra, the basin having an inferior side and a superior side;
   b. a lip extending radially from the rim of the basin and configured to contact the subject's abdomen or mons pubis, contoured to define a curved surface corresponding to a curvature of the subject's perineal region, and having an inferior end at the inferior end of the basin;
   c. a ridge disposed only on the inferior side of the basin and absent from the superior side of the basin, the ridge comprising a inferior edge, an anterior/superior edge forming a "V" with a curved apex when seen from above, the apex protruding dorsally away from the bowl of the basin on an inferior side of the basin, the ridge configured to create a seal by extending into the subject's vestibule of the vaginal opening; and
   d. a drain opening positioned on the basin for draining urine from the basin.

* * * * *